(12) United States Patent
Ebata

(10) Patent No.: US 12,364,464 B2
(45) Date of Patent: Jul. 22, 2025

(54) ULTRASOUND DIAGNOSTIC APPARATUS AND CONTROL METHOD OF ULTRASOUND DIAGNOSTIC APPARATUS

(71) Applicant: FUJIFILM Corporation, Tokyo (JP)

(72) Inventor: Tetsurou Ebata, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 34 days.

(21) Appl. No.: 18/496,826

(22) Filed: Oct. 27, 2023

(65) Prior Publication Data

US 2024/0122576 A1    Apr. 18, 2024

Related U.S. Application Data

(63) Continuation of application No. PCT/JP2022/010359, filed on Mar. 9, 2022.

(30) Foreign Application Priority Data

Apr. 30, 2021 (JP) ................. 2021-077689

(51) Int. Cl.
*A61B 8/00* (2006.01)
(52) U.S. Cl.
CPC ............ *A61B 8/5207* (2013.01); *A61B 8/466* (2013.01); *A61B 8/5276* (2013.01)
(58) Field of Classification Search
CPC ............ A61B 8/42–429; A61B 8/4461; A61B 8/4466; A61B 8/483; G01S 15/894; G01S 15/8945
See application file for complete search history.

(56) References Cited

U.S. PATENT DOCUMENTS

| 6,014,473 A | 1/2000 | Hossack et al. |
| 2016/0007972 A1* | 1/2016 | Nishiura ............ A61B 8/5269 600/437 |

(Continued)

FOREIGN PATENT DOCUMENTS

| CN | 103948399 A | 7/2014 |
| JP | 2001521404 A | 11/2001 |

(Continued)

OTHER PUBLICATIONS

Translation of JP-2020010747-A (Year: 2020).*

(Continued)

*Primary Examiner* — Carolyn A Pehlke
(74) *Attorney, Agent, or Firm* — Studebaker Brackett PLLC

(57) ABSTRACT

In an ultrasound diagnostic apparatus the of the present invention, a two-dimensional image generation unit generates a plurality of two-dimensional ultrasound images while shifting an angle or a position of a scanning plane using a transducer array in a state where an ultrasound probe is fixed by being in contact with an examination location of a subject. A motion determination unit sequentially calculates a similarity degree of at least two two-dimensional ultrasound images, and sequentially determines whether or not a motion of the ultrasound probe is within a predetermined reference value according to the similarity degree. Then, a three-dimensional image generation unit extracts the two-dimensional ultrasound images for which the motion of the ultrasound probe is determined to be within the reference value, to generate a three-dimensional ultrasound image, and a display control unit displays the three-dimensional ultrasound image on a monitor.

15 Claims, 10 Drawing Sheets

(56) References Cited

U.S. PATENT DOCUMENTS

2018/0028156 A1* 2/2018 Matsunaga .......... A61B 8/5207
2019/0083064 A1   3/2019 Nguyen et al.
2020/0337671 A1* 10/2020 Takada ................... A61B 8/42

FOREIGN PATENT DOCUMENTS

| JP | 2007330764 A |   | 12/2007 |
| --- | --- | --- | --- |
| JP | 201088585 A |   | 4/2010 |
| JP | 2010119511 A |   | 6/2010 |
| JP | 2010155031 A |   | 7/2010 |
| JP | 2013146454 A |   | 8/2013 |
| JP | 2017012607 A |   | 1/2017 |
| JP | 2019509856 A |   | 4/2019 |
| JP | 2019208592 A |   | 12/2019 |
| JP | 2020010747 A | * | 1/2020 |

OTHER PUBLICATIONS

International Search Report issued in PCT/JP2022/010359; mailed May 31, 2022.
International Preliminary Report On Patentability (Chapter I) and Written Opinion of the International Searching Authority issued in PCT/JP2022/010359; issued Oct. 24, 2023.

* cited by examiner

ULTRASOUND DIAGNOSTIC APPARATUS AND CONTROL METHOD OF ULTRASOUND DIAGNOSTIC APPARATUS

CROSS-REFERENCE TO RELATED APPLICATIONS

This application is a Continuation of PCT International Application No. PCT/JP2022/010359 filed on Mar. 9, 2022, which claims priority under 35 U.S.C. § 119(a) to Japanese Patent Application No. 2021-077689 filed on Apr. 30, 2021. The above applications are hereby expressly incorporated by reference, in their entirety, into the present application.

BACKGROUND OF THE INVENTION

1. Field of the Invention

The present invention relates to an ultrasound diagnostic apparatus and a control method of the ultrasound diagnostic apparatus which have a function of generating and displaying a two-dimensional ultrasound image and a three-dimensional ultrasound image.

2. Description of the Related Art

For example, JP2019-208592A, JP2019-509856A, and JP2013-146454A disclose an ultrasound diagnostic apparatus that can generate both two-dimensional ultrasound images and three-dimensional ultrasound images.

In order to generate the three-dimensional ultrasound image, for example, a certain amount of time is required to generate a plurality of two-dimensional ultrasound images by performing transmission and reception of ultrasound beams while shifting an angle or a position of a scanning plane in an elevation direction, and to generate a three-dimensional ultrasound image using the plurality of two-dimensional ultrasound images. Therefore, in a case where an ultrasound probe is moved by a user while a plurality of two-dimensional ultrasound images used for generating a three-dimensional ultrasound image are generated, an accurate three-dimensional ultrasound image cannot be generated.

SUMMARY OF THE INVENTION

For example, JP2019-208592A and JP2017-012607A disclose that the motion of the ultrasound probe is determined by calculating a movement vector and a similarity degree between frames of the two-dimensional ultrasound image and processing according to a determination result thereof is performed.

However, JP2019-208592A, JP2019-509856A, JP2013-146454A, and JP2017-012607A do not disclose selecting frames of the plurality of two-dimensional ultrasound images used for generating the three-dimensional ultrasound image on the basis of a calculation result of the movement vector or the similarity degree between frames of the ultrasound image.

An object of the present invention is to provide an ultrasound diagnostic apparatus and a control method of the ultrasound diagnostic apparatus which can generate an accurate three-dimensional ultrasound image even in a case where an ultrasound probe is moved.

In order to achieve the object, an aspect of the present invention provides an ultrasound diagnostic apparatus including an ultrasound probe having a transducer array; a two-dimensional image generation unit that generates a plurality of two-dimensional ultrasound images from reception signals obtained by sequentially performing transmission and reception of ultrasound beams while shifting an angle or a position of a scanning plane using the transducer array in a state where the ultrasound probe is fixed by being in contact with an examination location of a subject; a motion determination unit that sequentially calculates a similarity degree of at least two two-dimensional ultrasound images of the plurality of two-dimensional ultrasound images, and sequentially determines whether or not a motion of the ultrasound probe is within a predetermined reference value according to the similarity degree; a three-dimensional image generation unit that extracts the two-dimensional ultrasound images for which the motion of the ultrasound probe is determined to be within the reference value, from among the plurality of two-dimensional ultrasound images to generate a three-dimensional ultrasound image; a monitor; and a display control unit that displays the three-dimensional ultrasound image on the monitor.

Here, it is preferable that the three-dimensional image generation unit does not generate a current three-dimensional ultrasound image in a case where it is determined that the motion of the ultrasound probe exceeds the reference value, and the display control unit displays a past three-dimensional ultrasound image one before the current three-dimensional ultrasound image on the monitor in a case where the current three-dimensional ultrasound image is not generated.

In addition, it is preferable that the ultrasound diagnostic apparatus further includes a notification unit that notifies a user of a message representing that display of the three-dimensional ultrasound image is not updated, in a case where the current three-dimensional ultrasound image is not generated, and the display control unit displays the message on the monitor in a case where the past three-dimensional ultrasound image one before the current three-dimensional ultrasound image is displayed on the monitor.

In addition, it is preferable that, in a case where the similarity degree is equal to or greater than a predetermined threshold value, the motion determination unit determines that the motion of the ultrasound probe is within the reference value.

In addition, it is preferable that the ultrasound diagnostic apparatus further includes an observation target specifying unit that specifies an observation target present in each of the plurality of two-dimensional ultrasound images on the basis of each of the plurality of two-dimensional ultrasound images, and the motion determination unit changes the threshold value according to the observation target.

In addition, it is preferable that, in a case where the at least two two-dimensional ultrasound images include the two-dimensional ultrasound image in which a predetermined observation target is present, the motion determination unit changes the threshold value.

In addition, it is preferable that, in a case where the at least two two-dimensional ultrasound images include the two-dimensional ultrasound image in which a predetermined observation target is present, the motion determination unit changes the threshold value for the two-dimensional ultrasound image in which the predetermined observation target is present and the two-dimensional ultrasound images for a predetermined number of frames before and after the two-dimensional ultrasound image in which the predetermined observation target is present.

In addition, it is preferable that the motion determination unit changes the threshold value according to at least one of a type of the observation target, a depicting direction of the observation target, or an area of the observation target.

In addition, it is preferable that the motion determination unit obtains a similarity degree reference value on the basis of a similarity degree of the two-dimensional ultrasound images for a predetermined number of frames, and in a case where a current similarity degree for the similarity degree reference value falls below a predetermined threshold value, the motion determination unit determines that the motion of the ultrasound probe exceeds the reference value.

In addition, it is preferable that the motion determination unit stores the similarity degree reference value at a timing when the current similarity degree for the similarity degree reference value falls below the predetermined threshold value, and in a case where the current similarity degree for the stored similarity degree reference value falls within the predetermined threshold value in a period in which it is determined that the motion of the ultrasound probe is within the reference value, the motion determination unit determines that the ultrasound probe is stopped.

In addition, it is preferable that the motion determination unit changes a frame interval of the at least two two-dimensional ultrasound images according to a frame rate at a time of generating the plurality of two-dimensional ultrasound images.

In addition, it is preferable that the motion determination unit calculates the similarity degree while thinning out the two-dimensional ultrasound images for a predetermined number of frames at a predetermined frame interval, from the plurality of two-dimensional ultrasound images.

In addition, it is preferable that the ultrasound diagnostic apparatus further includes a motion sensor that is attached to the ultrasound probe, and the motion determination unit determines whether or not the motion of the ultrasound probe is within the reference value on the basis of the similarity degree, and a detection signal of the motion of the ultrasound probe output from the motion sensor.

Further, another aspect of the present invention provides a control method of an ultrasound diagnostic apparatus, the control method including a step of generating a plurality of two-dimensional ultrasound images from reception signals obtained by sequentially performing transmission and reception of ultrasound beams while shifting an angle or a position of a scanning plane using a transducer array of an ultrasound probe in a state where the ultrasound probe is fixed by being in contact with an examination location of a subject, via a two-dimensional image generation unit; a step of sequentially calculating a similarity degree of at least two two-dimensional ultrasound images of the plurality of two-dimensional ultrasound images, and sequentially determining whether or not a motion of the ultrasound probe is within a predetermined reference value according to the similarity degree, via a motion determination unit; a step of extracting the two-dimensional ultrasound images for which the motion of the ultrasound probe is determined to be within the reference value, from among the plurality of two-dimensional ultrasound images to generate a three-dimensional ultrasound image, via a three-dimensional image generation unit; and a step of displaying the three-dimensional ultrasound image on a monitor via a display control unit.

In the present invention, the similarity degree between frames of the two-dimensional ultrasound images is calculated, whether or not the motion of the ultrasound probe is within the reference value is determined according to the similarity degree, the two-dimensional ultrasound images for which the motion of the ultrasound probe is determined to be within the reference value are extracted, and the three-dimensional ultrasound image is generated. As a result, according to the present invention, even in a case where the ultrasound probe is moved by the user, an accurate three-dimensional ultrasound image can be generated by extracting the two-dimensional ultrasound images for which the motion of the ultrasound probe is determined to be within the reference value.

DESCRIPTION OF THE PREFERRED EMBODIMENTS

Hereinafter, an ultrasound diagnostic apparatus and a control method of the ultrasound diagnostic apparatus according to an embodiment of the present invention will be described in detail on the basis of preferred embodiments illustrated in the accompanying drawings.

Figure 1:
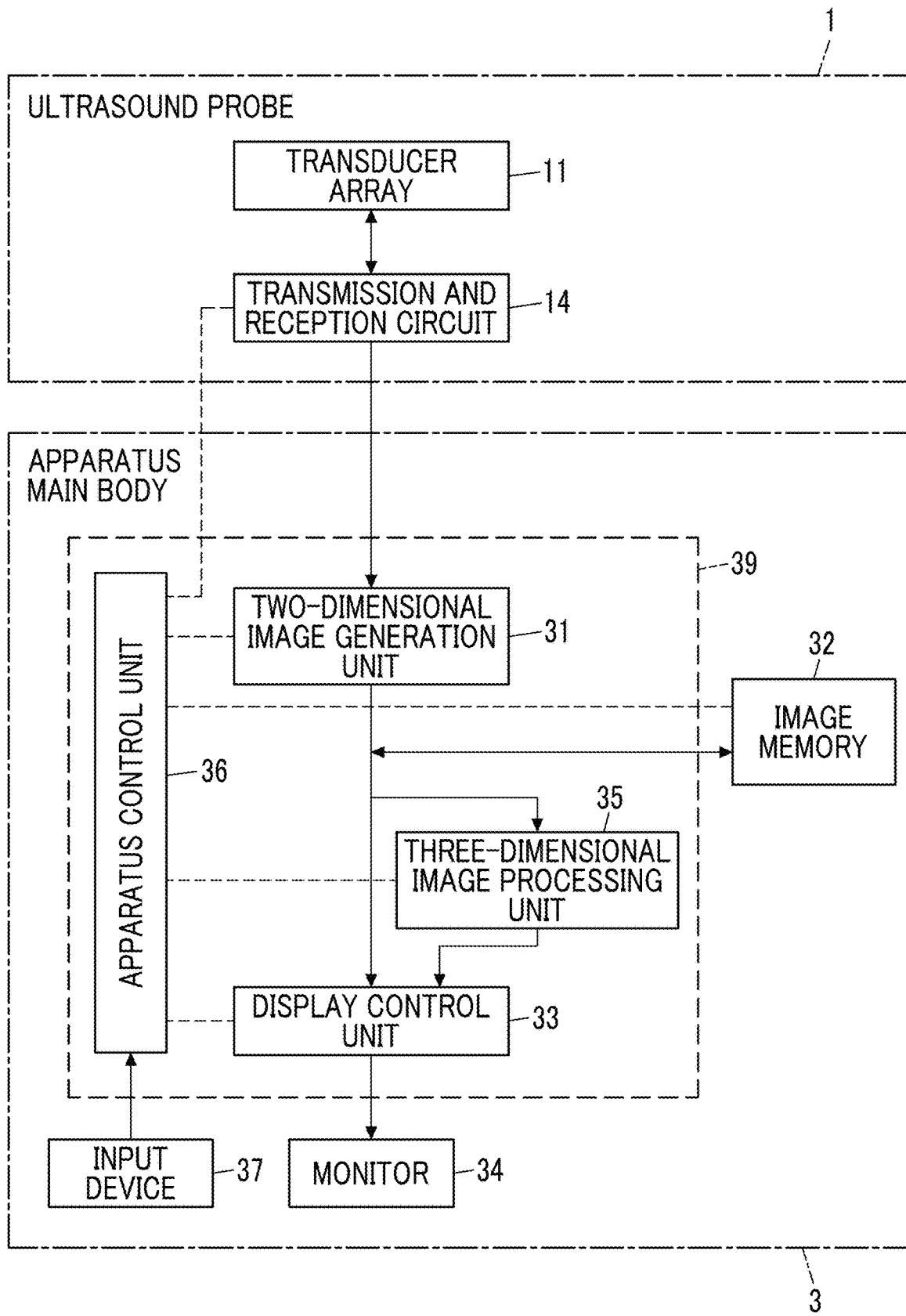
FIG. 1 is a block diagram of an embodiment illustrating a configuration of an ultrasound diagnostic apparatus of the present invention.

FIG. 1 is a block diagram of an embodiment illustrating a configuration of an ultrasound diagnostic apparatus according to the embodiment of the present invention. The ultrasound diagnostic apparatus illustrated in FIG. 1 is a stationary ultrasound diagnostic apparatus, and includes an ultrasound probe 1, and an apparatus main body 3 connected to the ultrasound probe 1.

The ultrasound probe 1 scans an examination location of a subject using an ultrasound beam, and outputs a sound ray signal corresponding to a two-dimensional ultrasound image of the examination location. As illustrated in FIG. 1, the ultrasound probe 1 includes a transducer array 11, and a transmission and reception circuit 14. The transducer array 11 and the transmission and reception circuit 14 are bidirectionally connected to each other. Further, an apparatus control unit 36 of the apparatus main body 3 which will be described later is connected to the transmission and reception circuit 14.

The transducer array 11 has a plurality of ultrasonic transducers arranged in a one-dimensional or two-dimensional manner. According to a drive signal supplied from the transmission and reception circuit 14, each of the transducers transmits an ultrasonic wave and receives a reflected wave from the subject to output an analog reception signal.

For example, each transducer is formed by using an element in which electrodes are formed at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

Figure 2:
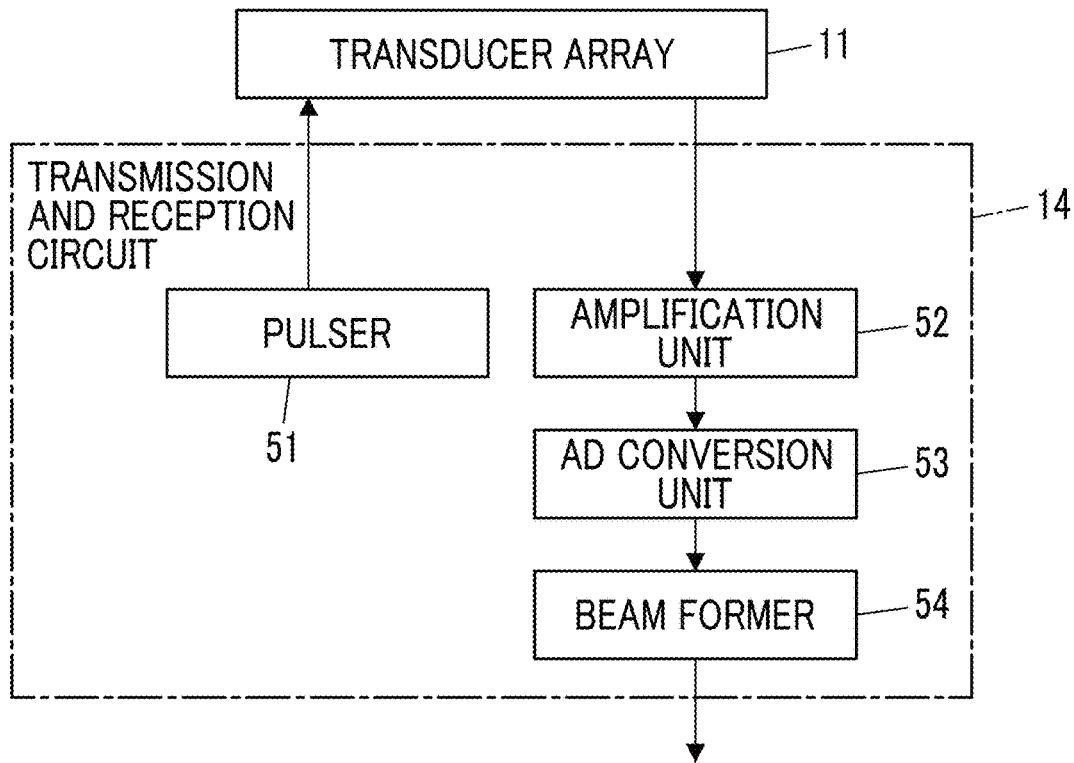
FIG. 2 is a block diagram of an embodiment illustrating a configuration of a transmission and reception circuit.

The transmission and reception circuit 14 causes the transducer array 11 to transmit the ultrasonic wave, and performs reception focusing processing on the reception signal output from the transducer array 11 that has received the ultrasound echo to generate a sound ray signal, under the control of the apparatus control unit 36. As illustrated in FIG. 2, the transmission and reception circuit 14 has a pulser 51 connected to the transducer array 11, and an amplification unit 52, an analog digital (AD) conversion unit 53, and a beam former 54 that are sequentially connected in series from the transducer array 11.

The pulser 51 includes, for example, a plurality of pulse generators, and the pulser 51 adjusts the amount of delay of each drive signal so that ultrasonic waves transmitted from the plurality of transducers of the transducer array 11 form an ultrasound beam on the basis of a transmission delay pattern selected by the apparatus control unit 36, and supplies the obtained signals to the plurality of transducers. Thus, in a case where a pulsed or continuous-wave voltage is applied to the electrodes of the transducers of the transducer array 11, the piezoelectric body expands and contracts to generate pulsed or continuous-wave ultrasonic waves from each transducer. From the combined wave of these ultrasonic waves, an ultrasound beam is formed.

The transmitted ultrasound beam is reflected by a target, for example, a site of the subject, and propagates toward the transducer array 11 of the ultrasound probe 1. Each transducer constituting the transducer array 11 expands and contracts by receiving the ultrasound echo propagating toward the transducer array 11 in this manner, to generate the reception signal that is an electric signal, and outputs the reception signal to the amplification unit 52.

The amplification unit 52 amplifies the signals input from each transducer constituting the transducer array 11, and transmits the amplified signals to the AD conversion unit 53. The AD conversion unit 53 converts the analog signal transmitted from the amplification unit 52 into digital reception data, and outputs the reception data to the beam former 54.

The beam former 54 performs so-called reception focusing processing in which addition is performed by giving delays to respective pieces of the reception data converted by the AD conversion unit 53 according to a sound speed distribution or a sound speed set on the basis of a reception delay pattern selected by the apparatus control unit 36. Through the reception focusing processing, a sound ray signal in which each piece of the reception data converted by the AD conversion unit 53 is phased and added and the focus of the ultrasound echo is narrowed is generated.

Next, the apparatus main body 3 generates the two-dimensional ultrasound image of the examination location of the subject on the basis of the sound ray signal generated by the ultrasound probe 1. Next, the apparatus main body 3 generates a three-dimensional ultrasound image of the examination location of the subject using the plurality of two-dimensional ultrasound images of the examination location of the subject. The apparatus main body 3 displays the two-dimensional ultrasound image and the three-dimensional ultrasound image of the examination location of the subject. As illustrated in FIG. 1, the apparatus main body 3 includes a two-dimensional image generation unit 31, an image memory 32, a three-dimensional image processing unit 35, a display control unit 33, a monitor (display unit) 34, an input device 37, and the apparatus control unit 36.

The two-dimensional image generation unit 31 is connected to the transmission and reception circuit 14, and the display control unit 33 and the monitor 34 are sequentially connected in series to the two-dimensional image generation unit 31. In addition, the image memory 32 is connected to the two-dimensional image generation unit 31, and each of the display control unit 33 and the three-dimensional image processing unit 35 is connected to the image memory 32. Furthermore, the display control unit 33 is connected to the three-dimensional image processing unit 35. The apparatus control unit 36 is connected to the two-dimensional image generation unit 31, the display control unit 33, the image memory 32, and the three-dimensional image processing unit 35, and the input device 37 is connected to the apparatus control unit 36.

The two-dimensional image generation unit 31 generates the two-dimensional ultrasound image (two-dimensional ultrasound image signal) of the examination location of the subject, from the reception signal obtained by performing transmission and reception of the ultrasound beams with respect to the examination location of the subject using the transducer array 11 of the ultrasound probe 1, in other words, from the sound ray signal generated from the reception signal by the transmission and reception circuit 14 in a state where the ultrasound probe 1 is in contact with the examination location of the subject, under the control of the apparatus control unit 36.

Figure 7A:
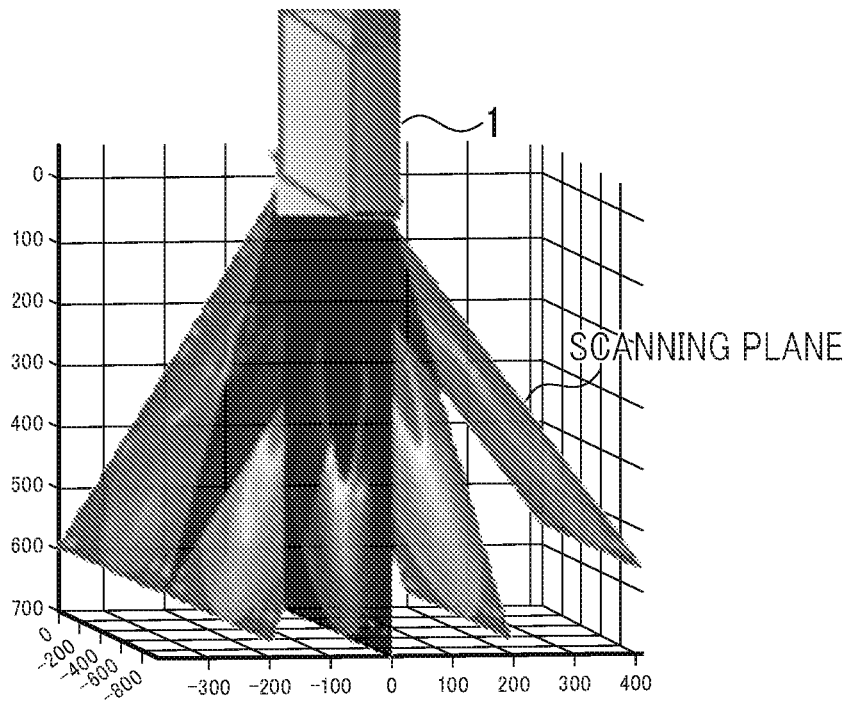
FIG. 7A is a conceptual diagram of an embodiment illustrating a state in which an angle of a scanning plane is shifted.
Figure 7B:
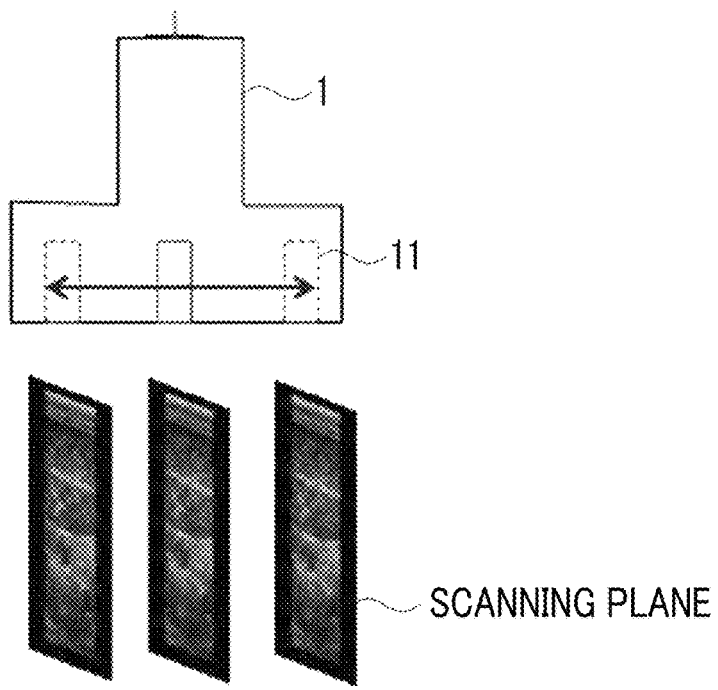
FIG. 7B is a conceptual diagram of an embodiment illustrating a state in which a position of a scanning plane is shifted.

In addition, the two-dimensional image generation unit 31 generates the plurality of two-dimensional ultrasound images with different angles or positions of the scanning plane from the reception signal obtained by sequentially performing the transmission and reception of the ultrasound beams while shifting the angle or position of the scanning plane in an elevation direction using the transducer array 11 as illustrated in FIGS. 7A and 7B, in a state where the ultrasound probe 1 is fixed by being in contact with the examination location of the subject, that is, in a stationary state where the ultrasound probe 1 is not moved. The plurality of two-dimensional ultrasound images are set as one set, and one three-dimensional ultrasound image (three-dimensional ultrasound image signal) is generated using one set of the plurality of two-dimensional ultrasound images. Here, the angle of the scanning plane means the inclination of the scanning plane with respect to a vertical direction. In addition, shifting the angle of the scanning plane in the elevation direction means increasing the inclination of the scanning plane with respect to the vertical direction, toward the elevation direction.

Figure 3:
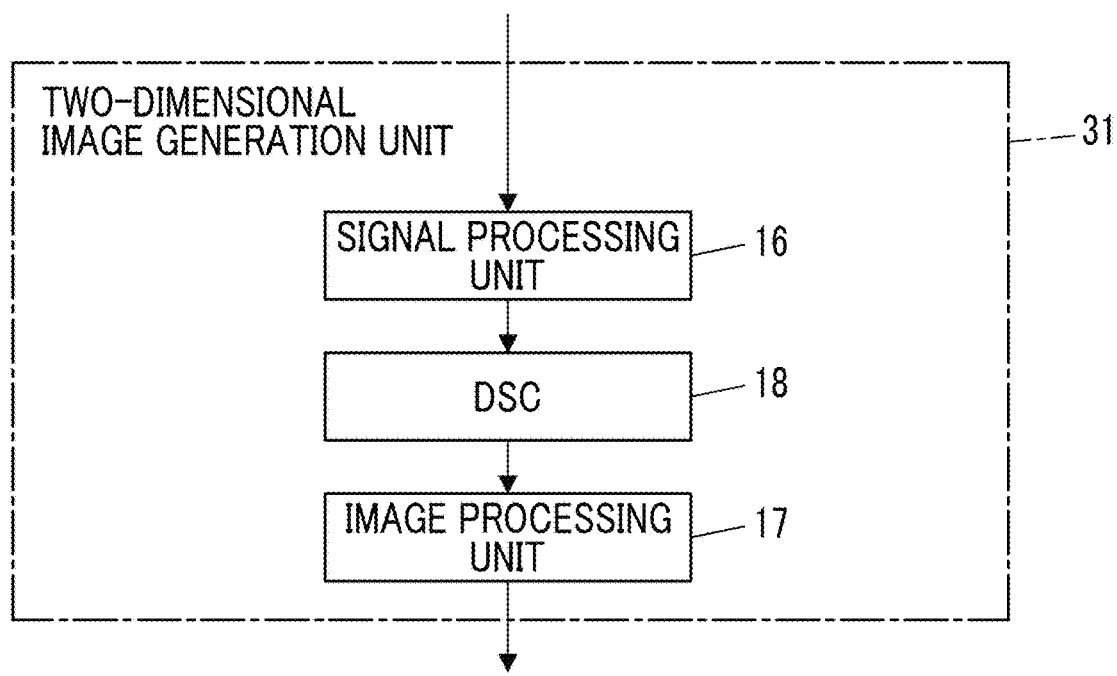
FIG. 3 is a block diagram of an embodiment illustrating a configuration of a two-dimensional image generation unit.

As illustrated in FIG. 3, the two-dimensional image generation unit 31 has a configuration in which a signal processing unit 16, a digital scan converter (DSC) 18, and an image processing unit 17 are sequentially connected in series.

The signal processing unit 16 generates image information data corresponding to the two-dimensional ultrasound image on the basis of the sound ray signal generated by the transmission and reception circuit 14. More specifically, the signal processing unit 16 generates the image information data representing tomographic image information regarding tissues inside the subject, by performing envelope detection processing after signal processing on the sound ray signal generated by the beam former 54 of the transmission and reception circuit 14, and then performing correction of the attenuation caused by the propagation distance according to the depth of the reflection position of the ultrasonic wave, for example.

The DSC 18 raster-converts the image information data generated by the signal processing unit 16 into an image signal according to a normal television signal scanning method.

The image processing unit 17 performs various kinds of image processing such as brightness correction, gradation correction, sharpness correction, image size correction, refresh rate correction, scanning frequency correction, and color correction according to a display format of the monitor 34, on the image signal input from the DSC 18 to generate the two-dimensional ultrasound image, and then outputs the two-dimensional ultrasound image on which the image processing has been performed, to the image memory 32 and the display control unit 33.

The image memory 32 is a memory that holds two-dimensional ultrasound images of the series of a plurality of frames, which are generated for each examination by the two-dimensional image generation unit 31, under the control of the apparatus control unit 36. For example, in a case where the three-dimensional ultrasound image is generated, as described above, the plurality of two-dimensional ultrasound images with different angles or positions of the scanning plane are generated by the two-dimensional image generation unit 31, and the plurality of two-dimensional ultrasound images are held in the image memory 32.

Here, as the image memory 32, recording media such as a flash memory, a hard disk drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), an external server, or the like can be used.

Figure 4:
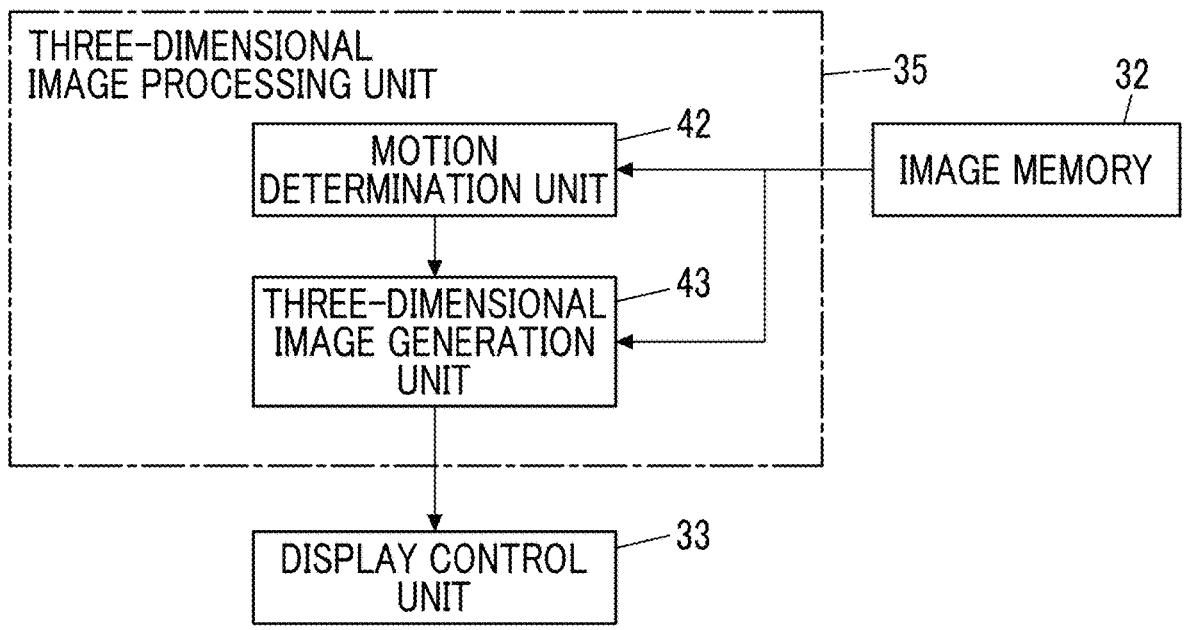
FIG. 4 is a block diagram of an embodiment illustrating a configuration of a three-dimensional image processing unit.

The three-dimensional image processing unit 35 performs various kinds of processing for generating the three-dimensional ultrasound image of the examination location of the subject using the plurality of two-dimensional ultrasound images held in the image memory 32, under the control of the apparatus control unit 36. As illustrated in FIG. 4, the three-dimensional image processing unit 35 includes a motion determination unit 42, and a three-dimensional image generation unit 43.

Each of the motion determination unit 42 and the three-dimensional image generation unit 43 is connected to the image memory 32. The three-dimensional image generation unit 43 is connected to the motion determination unit 42, and the display control unit 33 is connected to the three-dimensional image generation unit 43.

The motion determination unit 42 sequentially calculates the similarity degree of at least two two-dimensional ultrasound images among the plurality of two-dimensional ultrasound images held in the image memory 32, and sequentially determines whether or not the motion of the ultrasound probe 1 is within a predetermined reference value according to the similarity degree.

The method of calculating the similarity degree and the determination method of the motion are not particularly limited, and various methods known in the related art can be used. For example, the motion determination unit 42 calculates a score of the similarity degree and a score of the motion, and determines whether or not the motion of the ultrasound probe 1 is within the reference value according to whether or not the similarity degree is equal to or greater than a predetermined threshold value. In a case where the similarity degree is equal to or greater than the threshold value, that is in a case where the similarity degree is high, the motion determination unit 42 determines that the motion of the ultrasound probe 1 is within the reference value, that is, the ultrasound probe 1 is not moved by the user (examiner) of the ultrasound diagnostic apparatus.

For example, the motion determination unit 42 calculates each score of the similarity degree between adjacent frames of the two-dimensional ultrasound images, for one set of the plurality of two-dimensional ultrasound images for generating one three-dimensional ultrasound image. As in the ultrasound diagnostic apparatus of the present embodiment, in a case where the plurality of two-dimensional ultrasound images are generated by performing transmission and reception of ultrasound beams while shifting the angle or position of the scanning plane in the elevation direction, the similarity degree between adjacent frames of the two-dimensional ultrasound images is high, and always has similar scores.

However, it is expected that the similarity degree is significantly decreased in a case where the ultrasound probe 1 is moved by the user. Therefore, it is possible to accurately determine whether or not the ultrasound probe 1 is moved by the user, by observing the change of the similarity degree.

In a case of the ultrasound probe having a two-dimensional transducer array in the related art, for example, the two-dimensional ultrasound images are sequentially generated by performing the transmission and reception of ultrasound beams only in the vertical direction, and the motion between the frames of the two-dimensional ultrasound images is detected.

On the contrary, the ultrasound probe 1 of the present embodiment performs the transmission and reception of ultrasound beams while shifting the angle or position of the scanning plane in the elevation direction in a case of generating the three-dimensional ultrasound image. Therefore, since the time interval between the frames of the two-dimensional ultrasound images with the same angle or position of the scanning plane, for example, the time interval between the frames of the two-dimensional ultrasound images with the scanning plane in the vertical direction is long, in the method of calculating the similarity degree between the frames of the two-dimensional ultrasound images with the scanning plane in the vertical direction as in the related art, the motion cannot be accurately detected.

The three-dimensional image generation unit 43 extracts the two-dimensional ultrasound images for which the motion of the ultrasound probe 1 is determined to be within the reference value by the motion determination unit 42, from among the plurality of two-dimensional ultrasound images held in the image memory 32 to generate the three-dimensional ultrasound image.

The method of generating the three-dimensional ultrasound image is not particularly limited, and various methods of generating a three-dimensional ultrasound image from two or more two-dimensional ultrasound images known in the related art can be used.

The display control unit 33 displays various kinds of information on the monitor 34 under the control of the apparatus control unit 36. For example, the display control unit 33 performs predetermined processing on the two-dimensional ultrasound image generated by the two-dimensional image generation unit 31 or the two-dimensional ultrasound image held in the image memory 32, and displays the processed two-dimensional ultrasound image on the monitor 34. In addition, the display control unit 33 performs predetermined processing on the three-dimensional ultrasound image generated by the three-dimensional image generation unit 43, and displays the processed three-dimensional ultrasound image on the monitor 34.

The monitor 34 displays various kinds of information under the control of the display control unit 33. For example, the monitor 34 displays the two-dimensional ultrasound image generated by the two-dimensional image generation unit 31 or the two-dimensional ultrasound image held in the image memory 32, and the three-dimensional ultrasound image generated by the three-dimensional image generation unit 43. Examples of the monitor 34 include a display device such as a liquid crystal display (LCD), and an organic electroluminescence (EL) display.

The input device 37 receives various instructions input from the user. Although not particularly limited, the input device 37 includes various buttons, and a touch panel or the like through which various instructions are input by the user performing a touch operation.

The apparatus control unit 36 controls the ultrasound probe 1 and each unit of the apparatus main body 3 on the basis of a program stored in advance and an instruction or the like of the user input from the input device 37.

The two-dimensional image generation unit 31, the three-dimensional image processing unit 35, the display control unit 33, and the apparatus control unit 36 constitute a processor 39.

Figure 5:
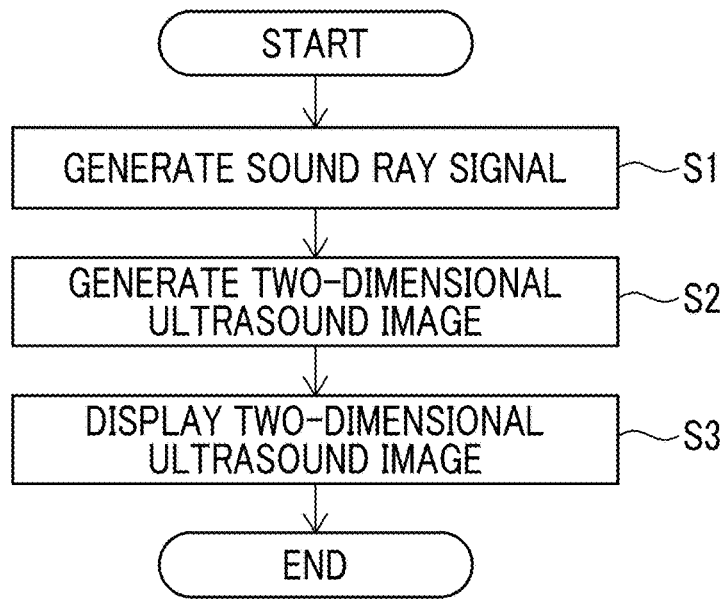
FIG. 5 is a flowchart of an embodiment illustrating an operation of an ultrasound diagnostic apparatus in a case of generating a two-dimensional ultrasound image.

Next, the operation of the ultrasound diagnostic apparatus in a case of generating the two-dimensional ultrasound image will be described with reference to the flowchart of FIG. 5.

First, in a case where the two-dimensional ultrasound image is generated, in a state where the ultrasound probe 1 is in contact with the examination location of the subject, the transmission of the ultrasonic waves is started and the sound ray signal is generated by the transmission and reception circuit 14, under the control of the apparatus control unit 36 (Step S1).

That is, the ultrasound beams are transmitted to the examination location of the subject from a plurality of transducers of the transducer array 11 according to the drive signals from the pulser 51.

Ultrasound echoes from the examination location based on the ultrasound beams transmitted from the pulser 51 are received by each transducer of the transducer array 11, and the reception signal as an analog signal is output from each transducer of the transducer array 11, which has received the ultrasound echo.

The reception signal output from each transducer of the transducer array 11 is amplified by the amplification unit 52, and is subjected to AD conversion by the AD conversion unit 53, and thereby the reception data is acquired.

By performing the reception focusing processing on the reception data by the beam former 54, the sound ray signal is generated.

Next, under the control of the apparatus control unit 36, the two-dimensional ultrasound image of the examination location of the subject is generated by the two-dimensional image generation unit 31 on the basis of the sound ray signal generated by the beam former 54 of the transmission and reception circuit 14 (Step S2).

That is, the sound ray signal generated by the beam former 54 is subjected to various kinds of signal processing by the signal processing unit 16, and the image information data representing tomographic image information regarding tissues inside the subject is generated.

The image information data generated by the signal processing unit 16 is raster-converted by the DSC 18, and is further subjected to various kinds of image processing by the image processing unit 17, and thus the two-dimensional ultrasound image is generated.

The two-dimensional ultrasound image generated by the image processing unit 17 is held in the image memory 32.

Next, under the control of the apparatus control unit 36, predetermined processing is performed on the two-dimensional ultrasound image generated by the image processing unit 17 or the two-dimensional ultrasound image held in the image memory 32 by the display control unit 33, and the processed two-dimensional ultrasound image is displayed on the monitor 34 (Step S3).

Figure 6:
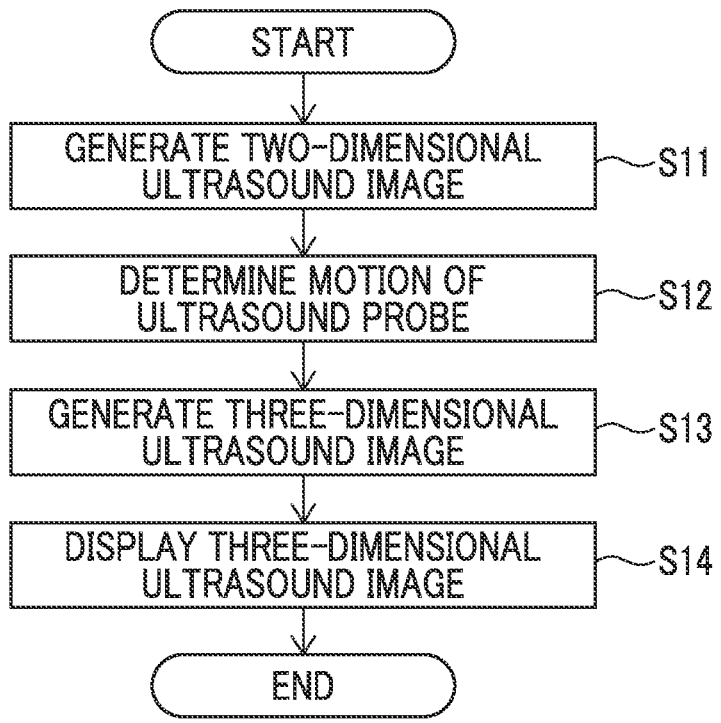
FIG. 6 is a flowchart of an embodiment illustrating an operation of an ultrasound diagnostic apparatus in a case of generating a three-dimensional ultrasound image.

Next, the operation of the ultrasound diagnostic apparatus in a case of generating the three-dimensional ultrasound image will be described with reference to the flowchart illustrated in FIG. 6.

In a case where the three-dimensional ultrasound image is generated, first, under the control of the apparatus control unit 36, the plurality of two-dimensional ultrasound images with different angles or positions of the scanning plane are generated by the two-dimensional image generation unit 31 from the reception signals obtained by sequentially performing the transmission and reception of the ultrasound beams while shifting the angle or position of the scanning plane using the transducer array 11 in a state where the ultrasound probe 1 is fixed by being in contact with the examination location of the subject (Step S11).

For example, in a case where the angle of the scanning plane is shifted using the one-dimensional transducer array 11, inside the housing of the ultrasound probe 1, the one-dimensional transducer array 11 is mechanically sequentially moved in the elevation direction along an arc centered on a rotation axis by a predetermined angle, and the transmission and reception of the ultrasound beams is sequentially performed while the angle of the scanning plane is shifted in the elevation direction (for example, refer to FIG. 2 of JP2013-146454A). As a result, the plurality of two-dimensional ultrasound images with different angles of the scanning plane are generated.

In a case where the position of the scanning plane is shifted using the one-dimensional transducer array 11, inside the housing of the ultrasound probe 1, the one-dimensional transducer array 11 is mechanically moved in parallel in the elevation direction by a predetermined distance, and the transmission and reception of the ultrasound beams is sequentially performed while the position of the scanning plane is sequentially shifted in the elevation direction (for example, refer to FIG. 7B). As a result, the plurality of two-dimensional ultrasound images with different positions of the scanning plane are generated.

In a case where the angle of the scanning plane is shifted using the two-dimensional transducer array 11, data of a transducer group extending in the azimuth direction of the two-dimensional transducer array 11 is delayed in the elevation direction, the scanning plane is sequentially steered by a predetermined angle, and the transmission and reception of the ultrasound beams is sequentially performed while the angle of the scanning plane is sequentially shifted in the elevation direction (for example, refer to FIG. 7A). As a result, the plurality of two-dimensional ultrasound images with different angles of the scanning plane are generated.

In a case where the position of the scanning plane is shifted using the two-dimensional transducer array 11, a transducer group extending in the azimuth direction of the two-dimensional transducer array 11 is sequentially selected in the elevation direction, and the transmission and reception of the ultrasound beams is sequentially performed while the position of the scanning plane is sequentially shifted in the elevation direction. As a result, the plurality of two-dimensional ultrasound images with different positions of the scanning plane are generated.

The method of shifting the angle or position of the scanning plane is not limited to the specific example described above, various methods for shifting the angle or position of the scanning plane in a state where the ultrasound probe 1 is fixed by being in contact with the examination location of the subject can be used.

Next, the two-dimensional ultrasound images generated by the two-dimensional image generation unit 31 are sequentially held in the image memory 32, under the control of the apparatus control unit 36. As a result, the plurality of two-dimensional ultrasound images with different angles or positions of the scanning plane are held in the image memory 32.

Next, in the three-dimensional image processing unit 35, various kinds of processing for generating the three-dimensional ultrasound image of the examination location of the subject are performed using the plurality of two-dimensional ultrasound images held in the image memory 32, under the control of the apparatus control unit 36.

That is, by the motion determination unit 42, the similarity degree of at least two two-dimensional ultrasound images among the plurality of two-dimensional ultrasound images is sequentially calculated, and whether or not the motion of the ultrasound probe 1 is within the predetermined reference value is sequentially determined according to the similarity degree (Step S12).

Then, by the three-dimensional image generation unit 43, the two-dimensional ultrasound images for which the motion of the ultrasound probe 1 is determined to be within the reference value by the motion determination unit 42 are extracted from among the plurality of two-dimensional ultrasound images, and the three-dimensional ultrasound image is generated (Step S13).

Next, by the display control unit 33, under the control of the apparatus control unit 36, the predetermined processing is performed on the three-dimensional ultrasound image generated by the three-dimensional image generation unit 43, and the processed three-dimensional ultrasound image (static image) is displayed on the monitor 34 (Step S14).

Similarly, setting a plurality of two-dimensional ultrasound images with different angles or positions of the scanning plane as one set, generating a next set of a plurality of two-dimensional ultrasound images, generating a next three-dimensional ultrasound image using the next set of the plurality of two-dimensional ultrasound images, and displaying the next three-dimensional ultrasound image is displayed on the monitor 34 are sequentially repeated. As a result, a video of the three-dimensional ultrasound images is displayed on the monitor 34.

In the ultrasound diagnostic apparatus of the present embodiment, the similarity degree between frames of the two-dimensional ultrasound images is calculated, whether or not the motion of the ultrasound probe 1 is within the reference value is determined according to the similarity degree, the two-dimensional ultrasound images for which the motion of the ultrasound probe 1 is determined to be within the reference value are extracted, and the three-dimensional ultrasound image is generated. As a result, even in a case where the ultrasound probe 1 is moved by the user, an accurate three-dimensional ultrasound image can be generated by extracting the two-dimensional ultrasound images for which the motion of the ultrasound probe 1 is determined to be within the reference value.

In a case where it is determined that the motion of the ultrasound probe 1 exceeds the reference value for the current set of the plurality of two-dimensional ultrasound images, the three-dimensional image generation unit 43 may not generate the current three-dimensional ultrasound image.

In a case where the current three-dimensional ultrasound image is not generated by the three-dimensional image generation unit 43, the display control unit 33 may display the past three-dimensional ultrasound image that is one before the current three-dimensional ultrasound image, on the monitor 34. In this case, the display of the three-dimensional ultrasound image is not updated, but the three-dimensional ultrasound image can be displayed without interruption.

Figure 8:
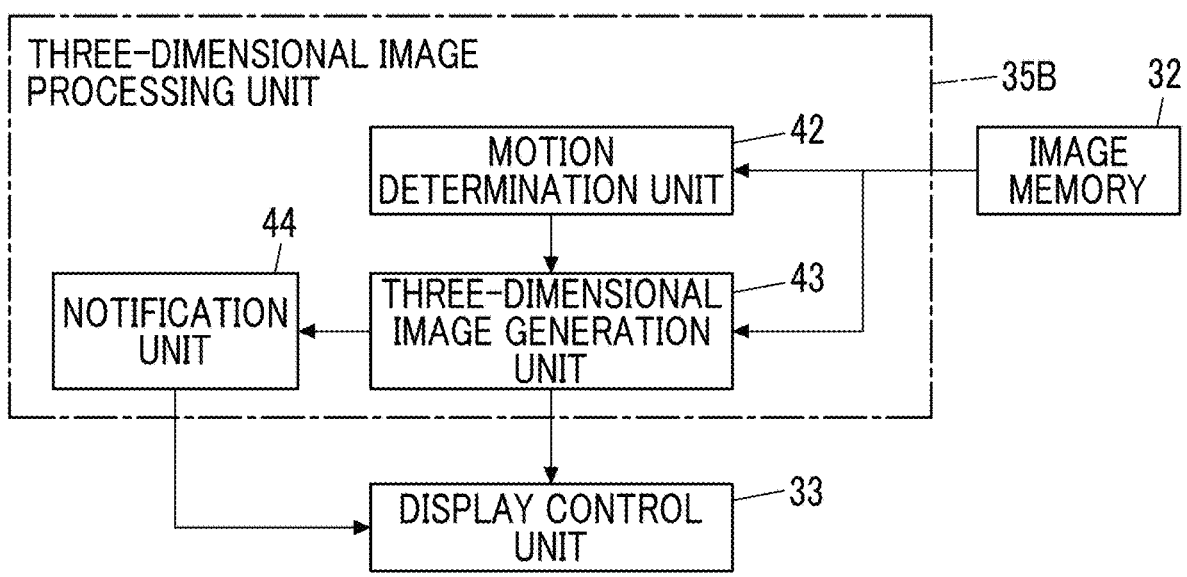
FIG. 8 is a block diagram of another embodiment illustrating a configuration of a three-dimensional image processing unit.

As illustrated in FIG. 8, a notification unit 44 may be provided in a three-dimensional image processing unit 35B, and in a case where the current three-dimensional ultrasound image is not generated, a message representing that the display of the three-dimensional ultrasound image is not updated may be notified to the user by the notification unit 44.

In FIG. 8, the notification unit 44 is connected to the three-dimensional image generation unit 43, and the display control unit 33 is connected to the notification unit 44.

In a case where the past three-dimensional ultrasound image one before the current three-dimensional ultrasound image is displayed on the monitor 34, the display control unit 33 may display a message such as "An accurate three-dimensional ultrasound image may not be displayed because the probe has been moved by the user." on the monitor 34 under the control of the notification unit. As a result, it is possible for the user to know that an accurate three-dimensional ultrasound image may not be displayed.

As the method of notifying the user of the message, a message may be displayed on the monitor 34 under the control of the notification unit as described above, a voice for reading a message may be output from a speaker (not illustrated), or both the display of the message and the voice output may be performed at the same time.

Figure 9:
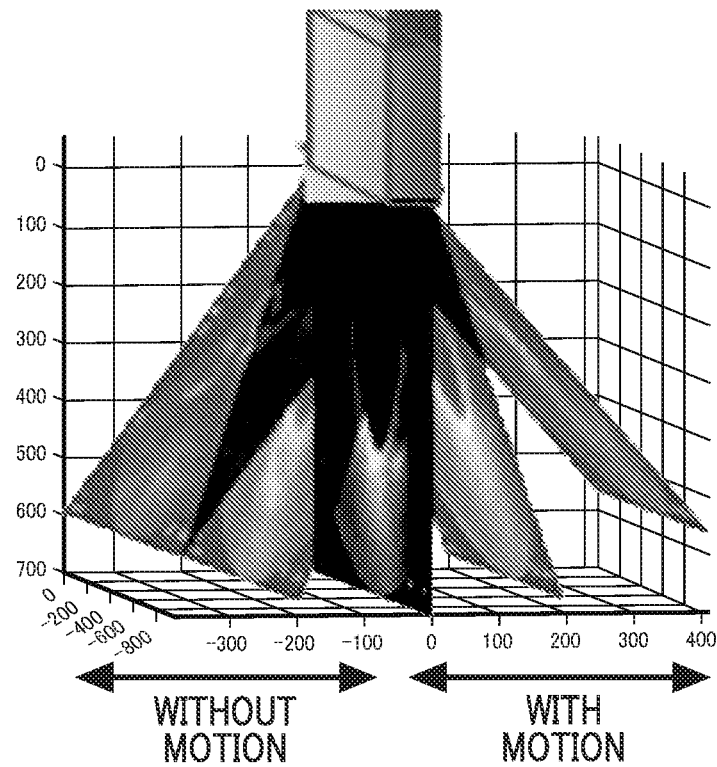
FIG. 9 is a conceptual diagram of an embodiment illustrating a state of an ultrasound probe with a motion and without a motion.

Alternatively, in a case where it is determined that the motion of the ultrasound probe 1 exceeds the reference value, as illustrated in FIG. 9, the three-dimensional image generation unit 43 may extract the two-dimensional ultrasound images, for which the determination "without motion" is made before a time point when the determination "with motion" is made, from among the plurality of two-dimensional ultrasound images generated with the plurality of scanning planes, to generate a partial three-dimensional ultrasound image. In other words, the two-dimensional ultrasound images before it is determined that the motion of the ultrasound probe 1 exceeds the reference value, that is, the two-dimensional ultrasound images for which the motion of the ultrasound probe 1 is determined to be within the reference value may be extracted, and a partial three-dimensional ultrasound image may be generated.

In this case, the display control unit 33 displays the partial three-dimensional ultrasound image on the monitor 34. As a result, it is possible to display a three-dimensional ultrasound image without interruption, although the image is not a complete three-dimensional ultrasound image.

The method of determining the similarity degree, in other words, the method of determining the motion of the ultrasound probe 1 may be changed according to an observation target present in the two-dimensional ultrasound image, for example, organs such as the heart and the blood vessel.

Figure 10:
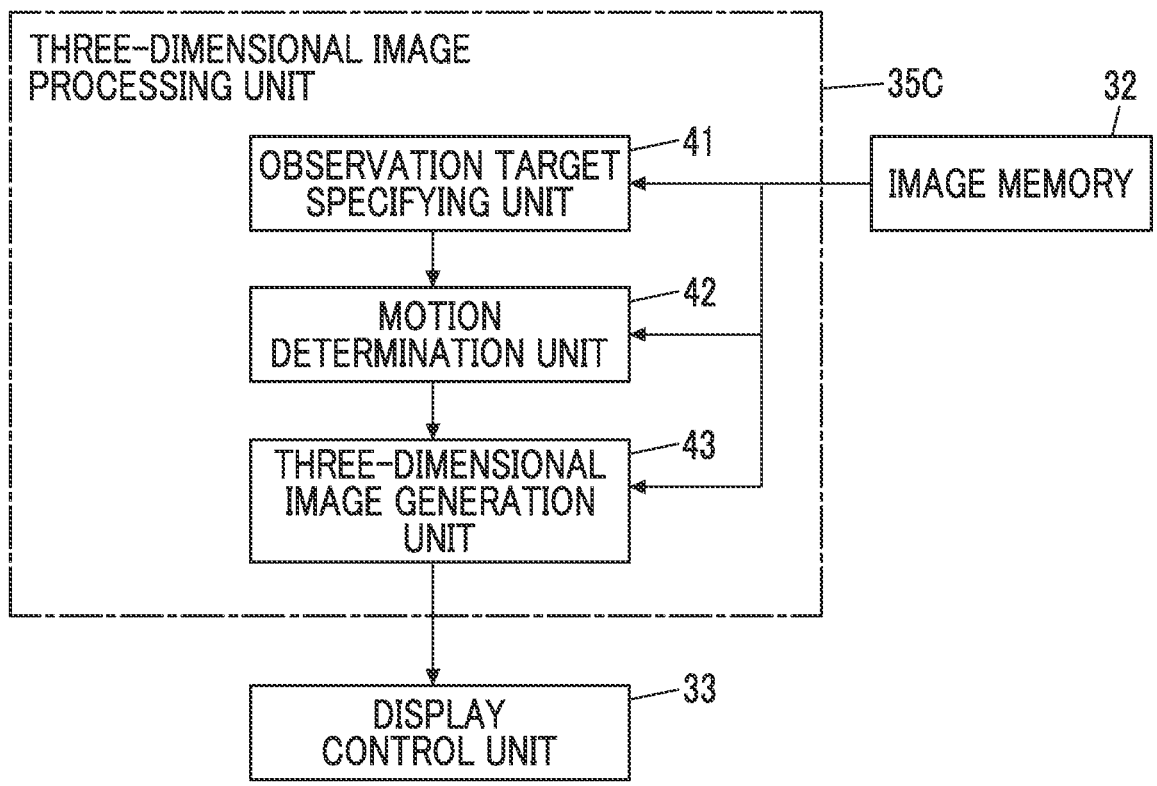
FIG. 10 is a block diagram of another embodiment illustrating a configuration of a three-dimensional image processing unit.

That is, as illustrated in FIG. 10, an observation target specifying unit 41 may be provided in a three-dimensional image processing unit 35C, and an observation target present in each of the plurality of two-dimensional ultrasound images is specified by the observation target specifying unit 41 on the basis of each of the plurality of two-dimensional ultrasound images held in the image memory 32.

In FIG. 10, the observation target specifying unit 41 is connected to the image memory 32, and the motion determination unit 42 is connected to the observation target specifying unit 41.

The method of specifying the observation target is not particularly limited, but various methods of specifying the observation target from the two-dimensional ultrasound image known in the related art, such as a method using a determination model generated by machine learning and a method using template matching can be used.

The motion determination unit 42 may change the threshold value of the similarity degree according to the observation target specified by the observation target specifying unit. For example, in a case where at least two two-dimensional ultrasound images used for calculating the similarity degree include two-dimensional ultrasound image in which the predetermined observation target such as the heart and the blood vessel is present, the motion determination unit 42 changes the threshold value of the similarity degree.

Figure 11:
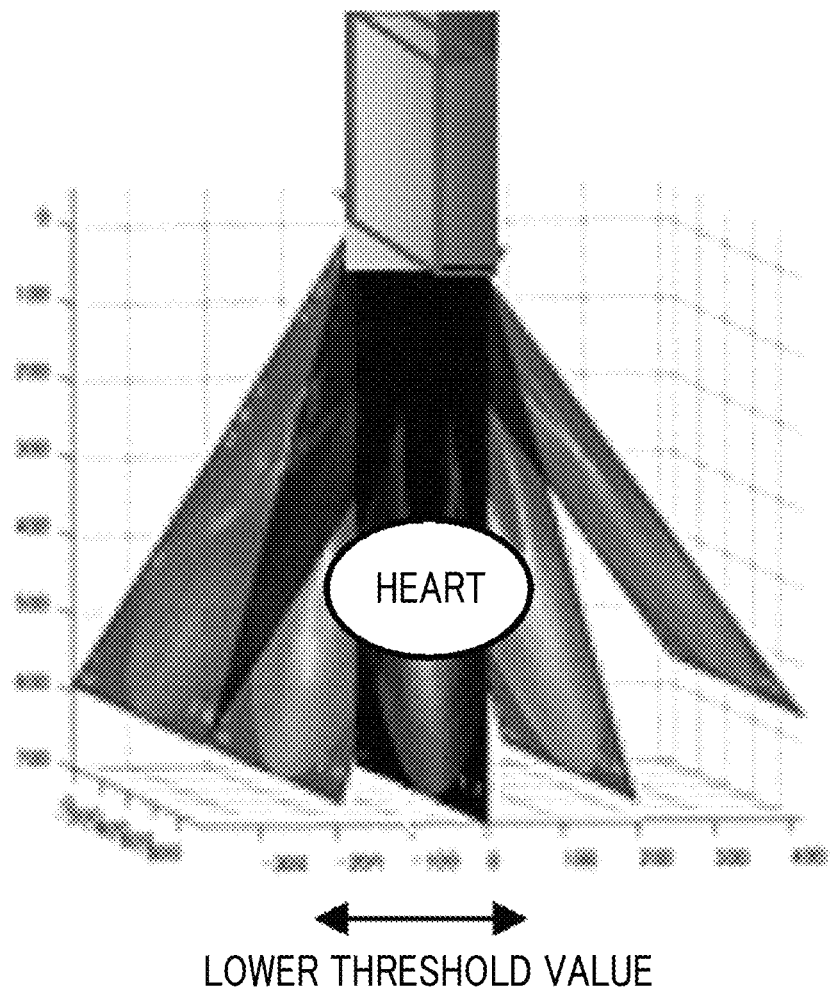
FIG. 11 is a conceptual diagram of an embodiment illustrating a state of lowering a threshold value in a case of calculating a similarity degree between frames of a two-dimensional ultrasound image in which a heart is present.

For example, in a case of depicting the heart using the ultrasound diagnostic apparatus, even in a case where the ultrasound probe 1 is not moved by the user, the similarity degree between frames of the two-dimensional ultrasound images may be decreased due to the heartbeat. Accordingly, as illustrated in FIG. 11, the heart present in each of the plurality of two-dimensional ultrasound images is specified, and in a case where at least two two-dimensional ultrasound images used for calculating the similarity degree include the two-dimensional ultrasound image in which the heart is present, the threshold value in a case of calculating the similarity degree is lowered. As a result, it is possible to calculate the similarity degree in consideration of the influence of the heartbeat.

In addition, similarly, also in a case of depicting the observation target having a complicated structure such as a kidney, even in a state where the ultrasound probe 1 is not moved by the user, the similarity degree between frames of the two-dimensional ultrasound images may be decreased. Accordingly, the kidney is specified from the two-dimensional ultrasound image, and in a case where the kidney is present, the threshold value in a case of calculating the similarity degree is lowered. As a result, it is possible to reduce the risk of erroneously determining that there is a motion of the ultrasound probe 1, due to the decrease in the similarity degree even though the ultrasound probe 1 is stationary.

In addition, the structures around the heart may be changed due to the heartbeat, the range of frames of the two-dimensional ultrasound images for which the threshold value of the similarity degree with respect to the frame of the two-dimensional ultrasound image in which the heart is present is changed may be expanded.

That is, in a case where at least two two-dimensional ultrasound images used for calculating the similarity degree include the two-dimensional ultrasound image in which the predetermined observation target is present, the motion determination unit 42 may change the threshold value of the similarity degree for the two-dimensional ultrasound image in which the predetermined observation target is present and two-dimensional ultrasound images for a predetermined number of frames before and after the two-dimensional ultrasound image in which the predetermined observation target is present.

Specifically, in a case where the observation target specifying unit 41 determines that the predetermined observation target is present, the threshold value of the similarity degree is changed for the two-dimensional ultrasound images five frames of the observation target and before and after the observation target. As illustrated in FIG. 7B, in a case where transmission and reception of the ultrasound beams is performed while shifting the position of the scanning plane in the elevation direction using the transducer array 11, the threshold value of the similarity degree is lowered for the two-dimensional ultrasound images of frames corresponding to the observation target and 1 cm before and after the observation target, for example. In addition, as illustrated in FIG. 9, in a case where transmission and reception of the ultrasound beams is performed while shifting the angle of the scanning plane using the transducer array 11, the threshold value of the similarity degree is lowered for the two-dimensional ultrasound images of frames of the observation target and 10° before and after the observation target, for example.

In the ultrasound diagnostic apparatus, the change amount of the angle or position of the adjacent scanning planes is set as a parameter in a case of generating the plurality of two-dimensional ultrasound images used for generating the three-dimensional ultrasound image. Therefore, the motion determination unit 42 can acquire the parameter, and calculate the angle or distance before and after the observation target on the basis of the parameter in a case where the threshold value of the similarity degree is changed.

For example, in a case of depicting the blood vessel using the ultrasound diagnostic apparatus, the threshold value of the similarity degree may be changed according to a depicting direction of the blood vessel. In this case, in a case where a short-axis view of the blood vessel is depicted, the two-dimensional ultrasound images between the frames are changed little, and thus the threshold value of the similarity degree is not changed. On the other hand, in a case where a long-axis view of the blood vessel is depicted, the two-dimensional ultrasound images of the frames are changed, and thus the threshold value of the similarity degree is lowered.

In a case where the area of the observation target is small, even in a case where the observation target is changed between the frames of the two-dimensional ultrasound images, the influence on the similarity degree of the entire two-dimensional ultrasound image is small. Therefore, the threshold value of the similarity degree may be changed according to the area of the observation target with respect to the area of the entire two-dimensional ultrasound image. For example, in a case where the area of the observation target with respect to the area of the entire two-dimensional ultrasound image is equal to or less than the predetermined threshold value, the threshold value of the similarity degree is lowered.

In this manner, it is desirable that the motion determination unit 42 changes the threshold value according to at least one of the type of the observation target such as the heart and the blood vessel, the depicting direction of the observation target, or the area of the observation target.

Alternatively, the motion determination unit 42 stores past similarity degrees of the two-dimensional ultrasound images for a predetermined number of frames, for example, for past 20 frames or for the number of past frames corresponding to one second, calculated from the frame rate. Furthermore, for example, the motion determination unit 42 obtains the average value or median of the past similarity degrees or a value of what number from the top of the past similarity as a similarity degree reference value on the basis of the past similarity degree, and compares the similarity degree reference value with the current similarity degree. Here, in a case where the current similarity degree with respect to the similarity degree reference value falls below the predetermined threshold value, it may be determined that there is a motion of the ultrasound probe 1. Specifically, assuming a case where the similarity degree reference value and the current similarity degree completely match each other as 100%, for example, in a case where the current similarity degree falls below a predetermined percentage such as 80% with respect to the similarity degree reference value, the motion determination unit 42 may determine that the motion of the ultrasound probe 1 exceeds the reference value, that is, that there is a motion of the ultrasound probe 1. In other words, in a case where the current similarity degree is outside the range of the predetermined threshold value compared with the similarity degree reference value, it may be determined that there is a motion of the ultrasound probe 1.

Furthermore, the motion determination unit 42 stores the similarity degree reference value at a timing when it is determined that there is a motion of the ultrasound probe 1, as the similarity degree in the stationary state. Furthermore, in a period in which it is determined that the motion of the ultrasound probe 1 is within the reference value, that is, in a period in which it is determined that the ultrasound probe 1 is not moved, in a case where the current similarity degree with respect to the stored similarity degree reference value falls within the predetermined threshold value, the motion determination unit 42 may determine that the ultrasound probe 1 is stopped again. Specifically, assuming a case where the previously stored similarity degree in the stationary state and the current similarity degree completely match each other as 100%, in a case where the current similarity degree falls within the percentage of, for example, 80% with respect to the similarity degree in the stationary state, it may be determined that the ultrasound probe 1 is stopped again. In other words, even in a case where it is determined that there is a motion of the ultrasound probe 1, in a case where the current similarity degree falls within the range of the predetermined threshold value compared with the similarity degree reference value (the similarity degree in the stationary state) stored at that timing, it may be determined that the ultrasound probe 1 is stopped again.

When the plurality of two-dimensional ultrasound images are generated while shifting the angle or position of the scanning plane, in a case where the change amount of the angle or position of the scanning plane is extremely small, in other words, in a case where a temporal acquisition interval of each frame of the plurality of two-dimensional ultrasound images is extremely short, even in a case where the ultrasound probe 1 is moved by the user, it is conceivable that there is almost no difference between the two-dimensional ultrasound images between adjacent frames, and thus the similarity degree is increased.

Therefore, the motion determination unit 42 may change the frame interval of at least two two-dimensional ultrasound images used for calculating the similarity degree according to the change amount of the angle or position of the scanning plane, or the temporal acquisition interval of each frame of the plurality of two-dimensional ultrasound images, in other words, the frame rate at the time of generating the plurality of two-dimensional ultrasound images. That is, the frame interval is changed to be longer as the frame rate is increased.

For example, it is assumed that the parameter is set such that a steering angle is shifted in 31 steps from +15 degrees to −15 degrees in 1-degree increment in a case of a first mode, and a steering angle is shifted in 61 steps from +15 degrees to −15 degrees in 0.5-degree increments in a case of a second mode. In this manner, in the case of the second mode, the change amount of the angle or position of the scanning plane is extremely small. Therefore, in the case of the second mode, instead of calculating the similarity degree of the consecutive frames, intermediate frames may be thinned out from a plurality of consecutive frames, and the similarity degree may be calculated using the remaining frames. For example, instead of calculating the similarity degree of consecutive frames such as calculating the similarity degree of the two-dimensional ultrasound images of the n-th frame and the (n+1)-th frame, and then calculating the similarity degree of the two-dimensional ultrasound images of the (n+1)-th frame and the (n+2)-th frame, the intermediate frames are thinned out from the plurality of consecutive frames, and the similarity degree is calculated using the remaining two frames, for example, calculating the similarity degree of the two-dimensional ultrasound images of the n-th frame and the (n+3)-th frame, and calculating the similarity degree of the two-dimensional ultrasound images of the (n+4)-th frame and the (n+7)-th frame.

In addition, the motion determination unit 42 may calculate the similarity degree while thinning out the predetermined number of frames of the two-dimensional ultrasound images at a predetermined frame interval, from the plurality of two-dimensional ultrasound images.

For example, the similarity degree is calculated while thinning out a part of frames of the plurality of two-dimensional ultrasound images such as calculating the similarity degree of the two-dimensional ultrasound images of the n-th frame and the (n+1)-th frame, skipping the two-dimensional ultrasound image of the (n+2)-th frame, calculating the similarity degree of the two-dimensional ultrasound images of the (n+3)-th frame and the (n+4)-th frame, skipping the two-dimensional ultrasound image of the (n+5)-th frame, and calculating the similarity degree of the two-dimensional ultrasound images of the (n+6)-th frame and the (n+7)-th frame. As a result, it is possible to reduce the calculation load compared to the case where the similarity degree of the two-dimensional ultrasound images of all the frames is calculated.

In addition, the motion of the ultrasound probe 1 may be detected using a motion sensor.

Figure 12:
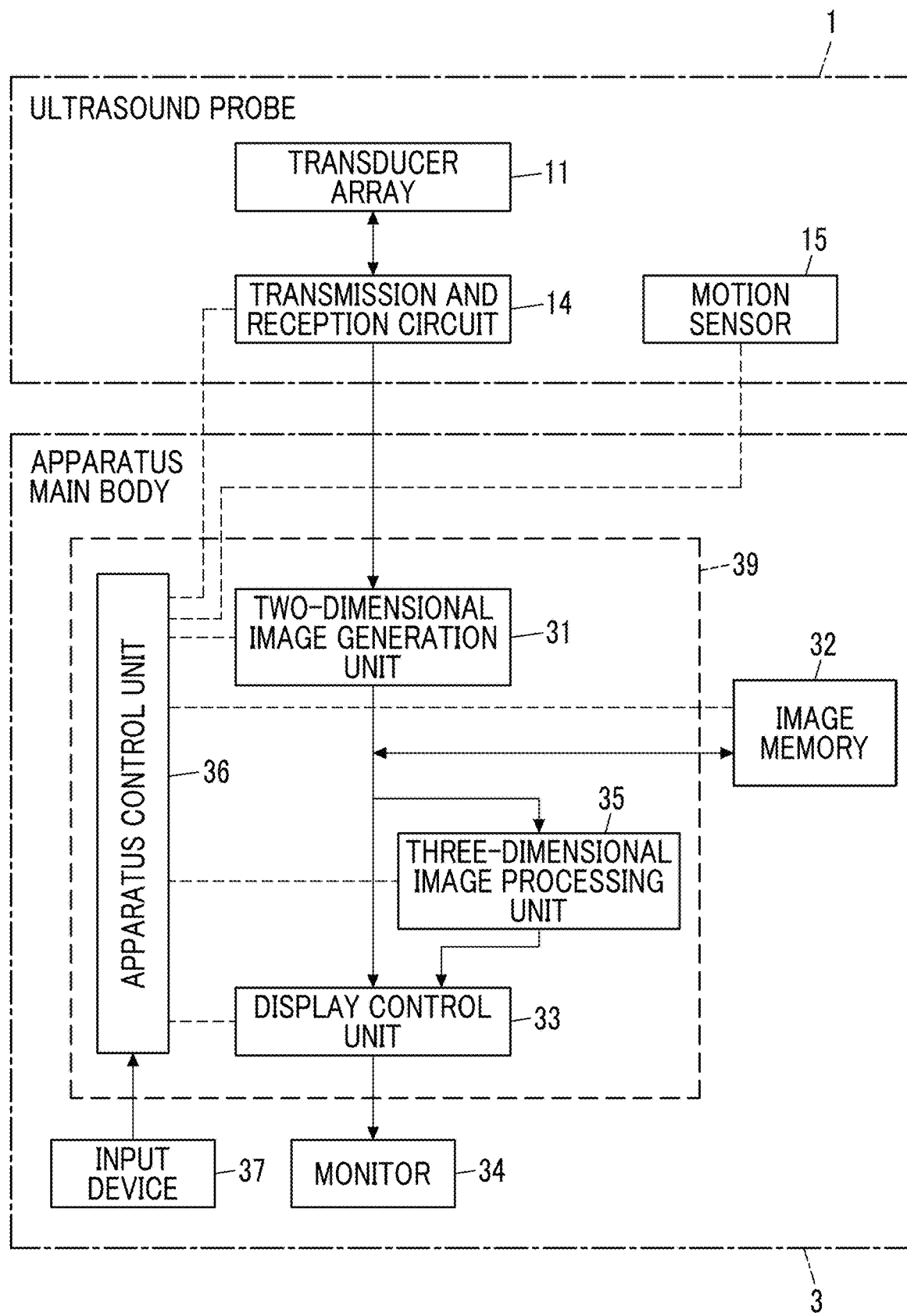
FIG. 12 is a block diagram of another embodiment illustrating a configuration of an ultrasound diagnostic apparatus of the present invention.

As illustrated in FIG. 12, under the control of the apparatus control unit 36, a motion sensor 15 detects the motion of the ultrasound probe 1, outputs the detection signal thereof, and is attached to the ultrasound probe 1. In addition, the apparatus control unit 36 of the apparatus main body 3 is connected to the motion sensor 15.

The detection signal of the motion sensor 15 includes a detection signal of the position (movement amount) in the movement direction such as parallel movement of the ultrasound probe 1 along the epidermis of the subject, a detection signal of the angle such as the inclination of the ultrasound probe 1, and the like.

In this case, the motion determination unit 42 determines whether or not the motion of the ultrasound probe 1 is within the reference value on the basis of the similarity degree and the detection signal of the motion of the ultrasound probe 1 output from the motion sensor 15.

The method of detecting the motion is not particularly limited, and various methods known in the related art can be used.

The motion of the ultrasound probe 1 includes a change of the position (movement amount) of the ultrasound probe 1 in the movement direction, a change of the angle of the ultrasound probe 1, and the like.

For example, it is possible to detect the change of the angle of the ultrasound probe 1 by using an acceleration sensor as the motion sensor 15. On the other hand, it is difficult for the acceleration sensor to detect the change of the position of the ultrasound probe 1 in the movement direction.

On the contrary, by using a magnetic sensor as the motion sensor 15, in a three-dimensional space of a magnetic field generated by a magnetic field generator, the position of the magnetic sensor, that is, the position of the ultrasound probe 1 in the movement direction, and the angle of the ultrasound probe 1 with respect to the vertical direction (inclination of the ultrasound probe 1 with respect to the vertical direction) can be detected by a magnetic field position detector on the basis of the position detection signal and the angle detection signal output from the magnetic sensor.

The motion determination unit 42 may determine the motion of the ultrasound probe 1 according to only the similarity degree, may determine the motion of the ultrasound probe 1 on the basis of only the detection signal of the motion sensor, or may determine the motion of the ultrasound probe 1 using both the similarity degree and the detection signal.

For example, the motion determination unit 42 can score each of the similarity degree and the detection signal of the motion sensor, and determine the presence or absence of the motion of the ultrasound probe 1 on the basis of the total value thereof.

Figure 13A:
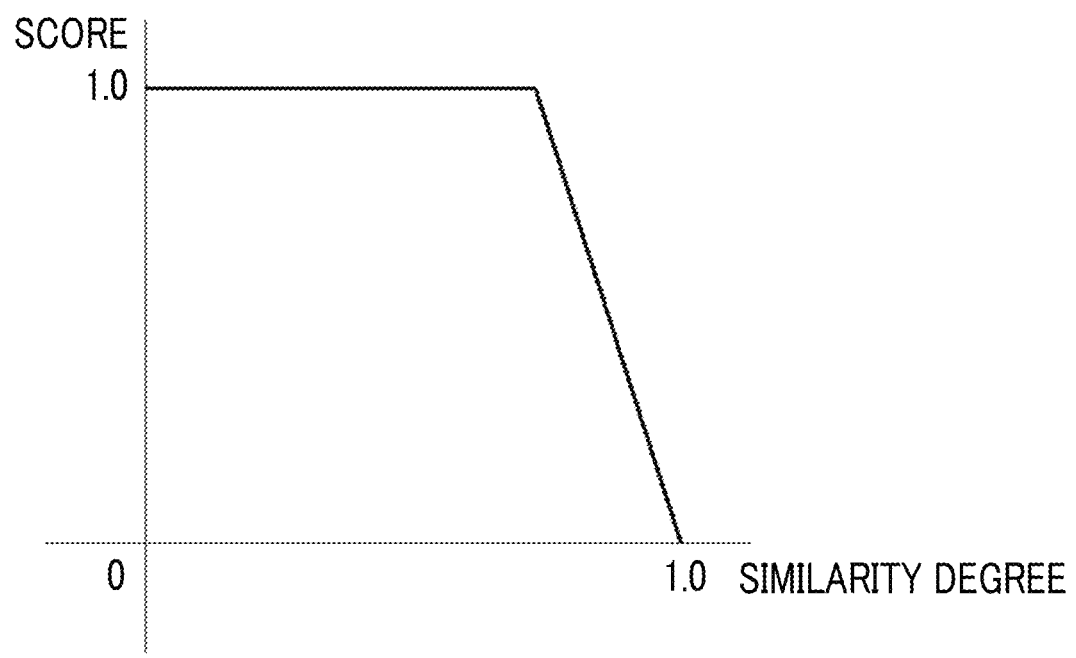
FIG. 13A is a graph of an embodiment of a conversion table illustrating a score for a similarity degree.
Figure 13B:
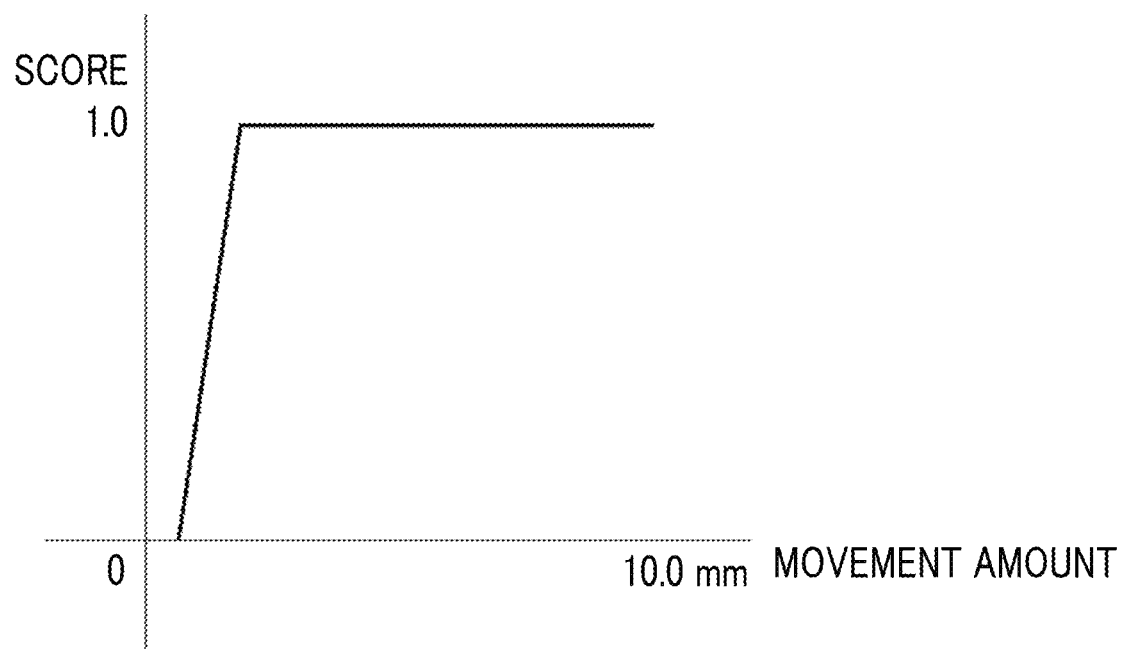
FIG. 13B is a graph of an embodiment of a conversion table illustrating a score for a detection signal of a movement amount by a motion sensor.
Figure 13C:
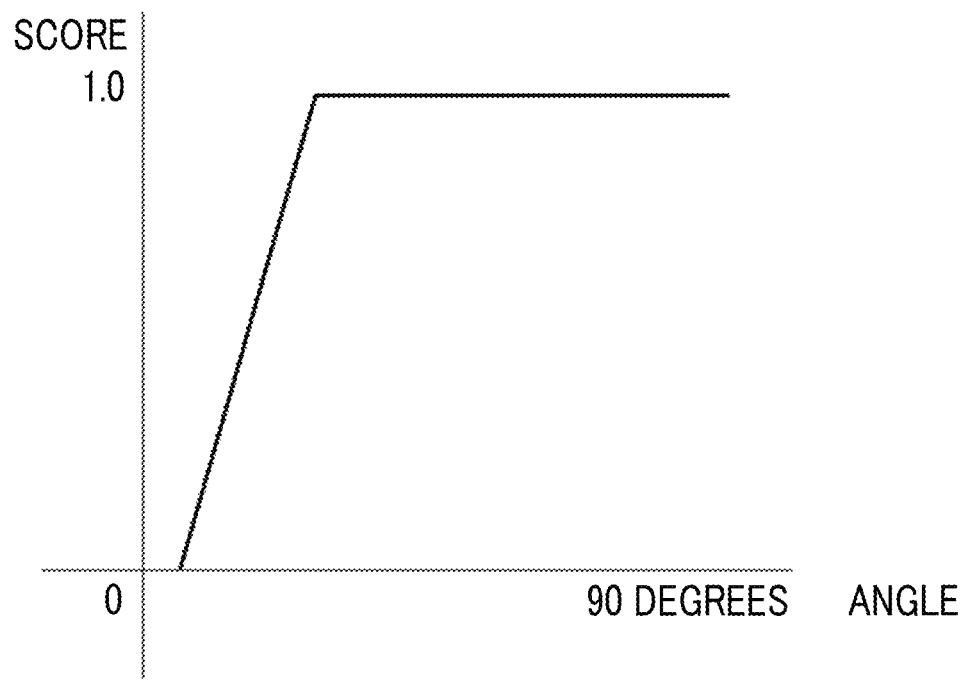
FIG. 13C is a graph of an embodiment of a conversion table illustrating a score for a detection signal of an angle by a motion sensor.

FIG. 13A is a graph of an embodiment of a conversion table illustrating the score for the similarity degree, FIG. 13B is a graph illustrating an embodiment of a conversion table illustrating the score for the detection signal of the movement amount by the motion sensor 15, and FIG. 13C is a graph illustrating an embodiment of a conversion table illustrating the score for the detection signal of the angle by the motion sensor 15. In the graphs illustrated in FIG. 13A, FIG. 13B, and FIG. 13C, the lateral axes respectively represent the similarity degree, the movement amount, and the angle, and the vertical axes represent the scores corresponding to the similarity degree, the movement amount, and the angle.

By using the conversion tables of the graphs illustrated in FIG. 13A, FIG. 13B, and FIG. 13C, the motion determination unit 42 calculates the score for the similarity degree, the score for the detection signal of the movement amount by the motion sensor 15, and the score for the detection signal of the angle by the motion sensor 15, and sums these three scores to calculate a final total score. The motion determination unit 42 compares the total score with the predetermined threshold value, determines that the ultrasound probe is moved in a case where the total score is equal to or greater than the threshold value, and determines that the ultrasound probe 1 is not moved in a case where the total score is less than the threshold value.

Note that the graphs of the conversion tables illustrated in FIG. 13A, FIG. 13B, and FIG. 13C are examples. In the graphs of FIG. 13A, FIG. 13B, and FIG. 13C, the upper limit of the score of each conversion table is set to 1.0, but can be set to any value. For example, in a case of putting emphasis on the score of the similarity degree, the upper limit value of the score of the conversion table for the similarity degree may be set to be greater than the upper limit value of the score of other conversion tables, and weighting may be performed. In addition, the shape of each graph is not limited to the shapes of the graphs illustrated in FIG. 13A, FIG. 13B, and FIG. 13C.

The presence or absence of the motion of the ultrasound probe 1 may be determined on the basis of each of the similarity degree and the motion sensor 15, and the motion of the ultrasound probe 1 may be finally determined by using the combination of the determination results.

For example, the final determination results in a case of determining the motion of the ultrasound probe 1 using the AND condition of the determination result by the similarity degree and the determination result by the motion sensor 15 are as follows.

a. similarity degree: without motion, motion sensor: without motion→final determination result: without motion b. similarity degree: with motion, motion sensor: without motion→final determination result: without motion c. similarity degree: without motion, motion sensor: with motion→final determination result: without motion d. similarity degree: with motion, motion sensor: with motion→final determination result: with motion Here, in a case of b described above, the final determination result is different from the determination result obtained on the basis of only the similarity degree.

In a case where the observation target is the heart, as described above, it is assumed that even in a case where the ultrasound probe 1 is not moved, the similarity degree of the two-dimensional ultrasound images between frames is decreased due to the heartbeat. On the contrary, the motion determination unit 42 can correctly determine that the ultrasound probe is without motion in a case where the ultrasound probe 1 is in the stationary state, by determining the motion of the ultrasound probe 1 using the determination result by the motion sensor 15.

On the other hand, the final determination results in a case of determining the motion of the ultrasound probe 1 using the OR condition of the determination result by the similarity degree and the determination result by the motion sensor 15 are as follows.

a. similarity degree: without motion, motion sensor: without motion→final determination result: without motion
    b. similarity degree: with motion, motion sensor: without motion→final determination result: with motion
    c. similarity degree: without motion, motion sensor: with motion→final determination result: with motion
    d. similarity degree: with motion, motion sensor: with motion→final determination result: with motion Here, in a case of c described above, the final determination result is different from the determination result obtained on the basis of only the similarity degree.

Figure 14:
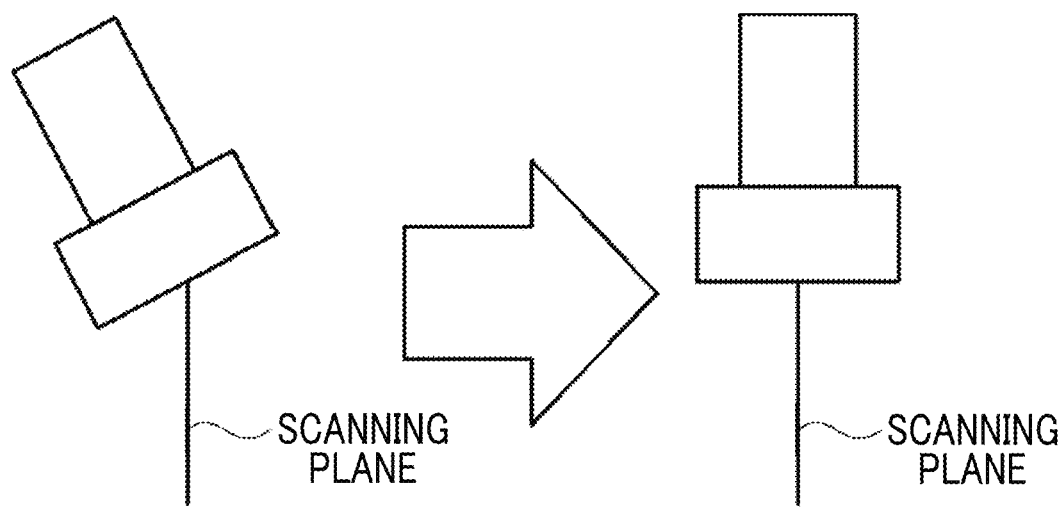
FIG. 14 is a conceptual diagram of an embodiment illustrating a state in which an ultrasound probe is rotated.

As illustrated in FIG. 14, in a case where the ultrasound probe 1 is manually rotated by the user at a speed close to the change of the angle at which the transducer array 11 is steered in the elevation direction, the angle of the scanning plane does not change much even though the ultrasound probe 1 is moved. In this case, the similarity degree is increased even though the ultrasound probe 1 is being moved. On the contrary, in a case where the determination result by the motion sensor 15 is that there is a motion, the motion determination unit 42 can correctly determine the motion of the ultrasound probe 1 by determining that the final determination result is that there is a motion.

Furthermore, the total value of the scores of the similarity degree and the motion sensor, and the combination (AND condition, OR condition) of the determination result by the similarity degree and the determination result by the motion sensor 15 to be adopted may be set in advance for each examination. For example, in a case of the heart, the AND condition of the determination result by the similarity degree and the determination result by the motion sensor 15 is adopted, in a case where the bladder, the OR condition of the determination result by the similarity degree and the determination result by the motion sensor 15 is adopted, and in other cases, the total value of the scores of the similarity degree and the motion sensor 15 is adopted.

The present invention is not limited to a stationary ultrasound diagnostic apparatus, and can be similarly applied to a portable ultrasound diagnostic apparatus in which an apparatus main body 3 is realized by a laptop terminal device, and a handheld ultrasound diagnostic apparatus in which an apparatus main body 3 is realized by a handheld terminal device such as a smartphone or a tablet personal computer (PC).

The ultrasound probe 1 and the apparatus main body 3 may be connected in a wired or wireless manner.

Further, the entire two-dimensional image generation unit 31 or only the signal processing unit 16 may be provided on the ultrasound probe 1 side, or provided on the apparatus main body 3 side.

In the apparatus of the embodiment of the present invention, the hardware configurations of the processing units executing various kinds of processing such as the transmission and reception circuit 14, the two-dimensional image generation unit 31, the display control unit 33, the three-dimensional image processing unit 35, and the apparatus control unit 36 may be dedicated hardware, or may be various processors or computers that execute programs.

The various processors include a central processing unit (CPU) as a general-purpose processor executing software (program) and functioning as various processing units, a programmable logic device (PLD) as a processor of which the circuit configuration can be changed after manufacturing such as a field programmable gate array (FPGA), and a dedicated electric circuit as a processor having a circuit configuration designed exclusively for executing specific processing such as an application specific integrated circuit (ASIC).

One processing unit may be configured by one of the various processors or may be configured by a combination of the same or different kinds of two or more processors, for example, a combination of a plurality of FPGAs or a combination of an FPGA and a CPU). Further, a plurality of processing units may be configured by one of various processors, or two or more of a plurality of processing units may be collectively configured by using one processor.

For example, there is a form where one processor is configured by a combination of one or more CPUs and software as typified by a computer, such as a server and a client, and this processor functions as a plurality of processing units. Further, there is a form where a processor realizing the functions of the entire system including a plurality of processing units by one integrated circuit (IC) chip as typified by a system on chip (SoC) or the like is used.

Furthermore, the hardware configurations of these various processors are more specifically electric circuitry where circuit elements, such as semiconductor elements, are combined.

The method of the embodiment of the present invention can be carried out, for example, by a program for causing a computer to execute each step of the method. Further, a computer-readable recording medium in which this program is recorded can also be provided.

The present invention has been described in detail, but the present invention is not limited to the above-described embodiments, and various improvements and changes may be made within a range not departing from the scope of the present invention.

EXPLANATION OF REFERENCES

1: ultrasound probe
3: apparatus main body
11: transducer array
14: transmission and reception circuit
15: motion sensor
16: signal processing unit
17: image processing unit
18: DSC
31: two-dimensional image generation unit
32: image memory
33: display control unit
34: monitor
35, 35B, 35C: three-dimensional image processing unit
36: apparatus control unit
37: input device
39: processor
41: observation target specifying unit
42: motion determination unit
43: three-dimensional image generation unit
44: notification unit
51: pulser
52: amplification unit
53: AD conversion unit
54: beam former

What is claimed is:
1. An ultrasound diagnostic apparatus comprising:
an ultrasound probe having a transducer array;
a monitor; and
a processor, wherein the processor is configured to:

generate a plurality of two-dimensional ultrasound images from reception signals obtained by sequentially performing transmission and reception of ultrasound beams while shifting an angle or a position of a scanning plane using the transducer array in a state where the ultrasound probe is fixed by being in contact with an examination location of a subject;

sequentially calculate a similarity degree of at least two two-dimensional ultrasound images of the plurality of two-dimensional ultrasound images, and sequentially determines whether or not a motion of the ultrasound probe is within a predetermined reference value according to the similarity degree;

extract the two-dimensional ultrasound images for which the motion of the ultrasound probe is determined to be within the reference value, from among the plurality of two-dimensional ultrasound images to generate a three-dimensional ultrasound image; and display the three-dimensional ultrasound image on the monitor, monitor, wherein in a case where the similarity degree is equal to or greater than a predetermined threshold value, the processor determines that the motion of the ultrasound probe is within the reference value, wherein the processor is configured to specify an observation target present in each of the plurality of two-dimensional ultrasound images on the basis of each of the plurality of two-dimensional ultrasound images, and wherein the processor changes the threshold value according to the observation target.

2. The ultrasound diagnostic apparatus according to claim 1, wherein the processor does not generate a current three-dimensional ultrasound image in a case where it is determined that the motion of the ultrasound probe exceeds the reference value, and the processor displays a past three-dimensional ultrasound image one before the current three-dimensional ultrasound image on the monitor in a case where the current three-dimensional ultrasound image is not generated.

3. The ultrasound diagnostic apparatus according to claim 2, wherein the processor is configured to notify a user of a message representing that display of the three-dimensional ultrasound image is not updated, in a case where the current three-dimensional ultrasound image is not generated, and wherein the processor displays the message on the monitor in a case where the past three-dimensional ultrasound image one before the current three-dimensional ultrasound image is displayed on the monitor.

4. The ultrasound diagnostic apparatus according to claim 1, wherein in a case where the at least two two-dimensional ultrasound images include the two-dimensional ultrasound image in which a predetermined observation target is present, the processor changes the threshold value.

5. The ultrasound diagnostic apparatus according to claim 1, wherein in a case where the at least two two-dimensional ultrasound images include the two-dimensional ultrasound image in which a predetermined observation target is present, the processor changes the threshold value for the two-dimensional ultrasound image in which the predetermined observation target is present and the two-dimensional ultrasound images for a predetermined number of frames before and after the two-dimensional ultrasound image in which the predetermined observation target is present.

6. The ultrasound diagnostic apparatus according to claim 1, wherein the processor changes the threshold value according to at least one of a type of the observation target, a depicting direction of the observation target, or an area of the observation target.

7. The ultrasound diagnostic apparatus according to claim 1, wherein the processor changes a frame interval of the at least two two-dimensional ultrasound images according to a frame rate at a time of generating the plurality of two-dimensional ultrasound images.

8. The ultrasound diagnostic apparatus according to claim 1, wherein the processor calculates the similarity degree while skipping the two-dimensional ultrasound images for a predetermined number of frames at a predetermined frame interval, from the plurality of two-dimensional ultrasound images.

9. The ultrasound diagnostic apparatus according to claim 2, wherein the processor obtains a similarity degree reference value on the basis of a similarity degree of the two-dimensional ultrasound images for a predetermined number of frames, and in a case where a current similarity degree for the similarity degree reference value falls below a predetermined threshold value, the processor determines that the motion of the ultrasound probe exceeds the reference value.

10. An ultrasound diagnostic apparatus comprising:
an ultrasound probe having a transducer array;
a monitor; and
a processor, wherein the processor is configured to:
generate a plurality of two-dimensional ultrasound images from reception signals obtained by sequentially performing transmission and reception of ultrasound beams while shifting an angle or a position of a scanning plane using the transducer array in a state where the ultrasound probe is fixed by being in contact with an examination location of a subject;

sequentially calculate a similarity degree of at least two two-dimensional ultrasound images of the plurality of two-dimensional ultrasound images, and sequentially determines whether or not a motion of the ultrasound probe is within a predetermined reference value according to the similarity degree;

extract the two-dimensional ultrasound images for which the motion of the ultrasound probe is determined to be within the reference value, from among the plurality of two-dimensional ultrasound images to generate a three-dimensional ultrasound image; and display the three-dimensional ultrasound image on the monitor, wherein the processor obtains a similarity degree reference value on the basis of a similarity degree of the two-dimensional ultrasound images for a predetermined number of frames, and in a case where a current similarity degree for the similarity degree reference value falls below a predetermined threshold value, the processor determines that the motion of the ultrasound probe exceeds the reference value, and wherein the processor stores the similarity degree reference value at a timing when the current similarity degree for the similarity degree reference value falls below the predetermined threshold value, and in a case where the current similarity degree for the stored similarity degree reference value falls within the predetermined threshold value in a period in which it is determined that the motion of the ultrasound probe is within the reference value, the processor determines that the ultrasound probe is stopped.

11. An ultrasound diagnostic apparatus comprising:
an ultrasound probe having a transducer array;
a motion sensor that is attached to the ultrasound probe;
a monitor; and
a processor, wherein the processor is configured to:
generate a plurality of two-dimensional ultrasound images from reception signals obtained by sequentially performing transmission and reception of ultrasound beams while shifting an angle or a position of a scanning plane using the transducer array in a state where the ultrasound probe is fixed by being in contact with an examination location of a subject;
sequentially calculate a similarity degree of at least two two-dimensional ultrasound images of the plurality of two-dimensional ultrasound images, and sequentially determines whether or not a motion of the ultrasound probe is within a predetermined reference value according to the similarity degree;
extract the two-dimensional ultrasound images for which the motion of the ultrasound probe is determined to be within the reference value, from among the plurality of two-dimensional ultrasound images to generate a three-dimensional ultrasound image; and
display the three-dimensional ultrasound image on the monitor,
wherein the processor determines whether or not the motion of the ultrasound probe is within the reference value on the basis of the similarity degree, and a detection signal of the motion of the ultrasound probe output from the motion sensor.

12. An ultrasound diagnostic apparatus comprising:
an ultrasound probe having a transducer array;
a monitor; and
a processor, wherein the processor is configured to:
generate a plurality of two-dimensional ultrasound images from reception signals obtained by sequentially performing transmission and reception of ultrasound beams while shifting an angle or a position of a scanning plane using the transducer array in a state where the ultrasound probe is fixed by being in contact with an examination location of a subject;
sequentially calculate a similarity degree of at least two two-dimensional ultrasound images of the plurality of two-dimensional ultrasound images, and sequentially determines whether or not a motion of the ultrasound probe is within a predetermined reference value according to the similarity degree;
extract the two-dimensional ultrasound images for which the motion of the ultrasound probe is determined to be within the reference value, from among the plurality of two-dimensional ultrasound images to generate a three-dimensional ultrasound image; and
display the three-dimensional ultrasound image on the monitor,
wherein the processor does not generate a current three-dimensional ultrasound image in a case where it is determined that the motion of the ultrasound probe exceeds the reference value, and
the processor displays a past three-dimensional ultrasound image one before the current three-dimensional ultrasound image on the monitor in a case where the current three-dimensional ultrasound image is not generated,
wherein in a case where the similarity degree is equal to or greater than a predetermined threshold value, the processor determines that the motion of the ultrasound probe is within the reference, value,
wherein the processor is configured to specify an observation target present in each of the plurality of two-dimensional ultrasound images on the basis of each of the plurality of two-dimensional ultrasound images, and
wherein the processor changes the threshold value according to the observation target.

13. The ultrasound diagnostic apparatus according to claim 12,
wherein in a case where the at least two two-dimensional ultrasound images include the two-dimensional ultrasound image in which a predetermined observation target is present, the processor changes the threshold value.

14. The ultrasound diagnostic apparatus according to claim 12,
wherein in a case where the at least two two-dimensional ultrasound images include the two-dimensional ultrasound image in which a predetermined observation target is present, the processor changes the threshold value for the two-dimensional ultrasound image in which the predetermined observation target is present and the two-dimensional ultrasound images for a predetermined number of frames before and after the two-dimensional ultrasound image in which the predetermined observation target is present.

15. An ultrasound diagnostic apparatus comprising:
an ultrasound probe having a transducer array;
a monitor; and
a processor, wherein the processor is configured to:
generate a plurality of two-dimensional ultrasound images from reception signals obtained by sequentially performing transmission and reception of ultrasound beams while shifting an angle or a position of a scanning plane using the transducer array in a state where the ultrasound probe is fixed by being in contact with an examination location of a subject;
sequentially calculate a similarity degree of at least two two-dimensional ultrasound images of the plurality of two-dimensional ultrasound images, and sequentially determines whether or not a motion of the ultrasound probe is within a predetermined reference value according to the similarity degree;
extract the two-dimensional ultrasound images for which the motion of the ultrasound probe is determined to be within the reference value, from among the plurality of two-dimensional ultrasound images to generate a three-dimensional ultrasound image; and
display the three-dimensional ultrasound image on the monitor,
wherein in a case where the similarity degree is equal to or greater than a predetermined threshold value, the processor determines that the motion of the ultrasound probe is within the reference value,
wherein the processor is configured to specify an observation target present in each of the plurality of two-dimensional ultrasound images on the basis of each of the plurality of two-dimensional ultrasound images, wherein the processor changes the threshold value according to the observation target, wherein in a case where the at least two two-dimensional ultrasound images include the two-dimensional ultrasound image in which a predetermined observation target is present, the processor changes the threshold value, and wherein the processor changes the threshold value according to at least one of a type of the observation target, a depicting direction of the observation target, or an area of the observation target.

* * * * *